US011214821B2

(12) United States Patent
Denney

(10) Patent No.: US 11,214,821 B2
(45) Date of Patent: Jan. 4, 2022

(54) REAGENTS AND METHODS OF USE WITH AUTOMATED ANALYZERS FOR OBTAINING A SPECIFIC GRAVITY INDEX FOR URINE

(71) Applicant: Vision Diagnostics, Inc., Branford, FL (US)

(72) Inventor: Jerry W. Denney, Branford, FL (US)

(73) Assignee: VISION DIAGNOSTICS, INC., Branford, FL (US)

(*) Notice: Subject to any disclaimer, the term of this patent is extended or adjusted under 35 U.S.C. 154(b) by 275 days.

(21) Appl. No.: 15/651,334

(22) Filed: Jul. 17, 2017

(65) Prior Publication Data
US 2018/0127799 A1 May 10, 2018

Related U.S. Application Data

(60) Provisional application No. 62/363,421, filed on Jul. 18, 2016.

(51) Int. Cl.
C12Q 1/34 (2006.01)
G01N 33/94 (2006.01)
C12Q 1/00 (2006.01)

(52) U.S. Cl.
CPC ........... C12Q 1/34 (2013.01); G01N 33/94 (2013.01); G01N 2333/938 (2013.01)

(58) Field of Classification Search
CPC ..... G01N 33/94; G01N 2333/938; C12Q 1/34
See application file for complete search history.

(56) References Cited

U.S. PATENT DOCUMENTS

| 4,318,709 A | * | 3/1982 | Falb | G01N 33/52 422/420 |
| 5,055,407 A | * | 10/1991 | Lau | G01N 33/52 436/2 |
| 5,055,447 A | * | 10/1991 | Palladino | A61K 38/1841 424/164.1 |
| 5,516,700 A | * | 5/1996 | Smith | C12Q 1/26 436/164 |

(Continued)

FOREIGN PATENT DOCUMENTS

EP 470652 A2 2/1992

OTHER PUBLICATIONS

Quiles, R. et al., "Automated Enzymatic Determination of Sodium in Serum," *Clin. Chem.*, 1993, pp. 500-503, vol. 39.

Primary Examiner — Rebecca M Fritchman
(74) Attorney, Agent, or Firm — Saliwanchik, Lloyd & Eisenschenk

(57) ABSTRACT

Reagents and methods for using automated laboratory equipment to determine whether the specific gravity of a urine sample is out of normal range as an indication of adulteration. The sodium (Na+) and potassium (K+) normally found in a urine sample can be used as markers. A sodium-potassium dependent β-galactosidase can be utilized with o-nitrophenylgalactoside (o-NPG) which is cleaved into o-nitrophenol, which turns the sample yellow. The sample can be analyzed by spectrophotometry methods utilized in most clinical analyzers at a pre-determined primary wavelength to obtain a Specific gravity Index (SGI). Measurements of the SGI that are outside a known normal range can indicate that the sample integrity has been compromised.

17 Claims, 2 Drawing Sheets

(56) References Cited

U.S. PATENT DOCUMENTS

| | | | | |
|---|---|---|---|---|
| 2002/0160439 A1* | 10/2002 | Anne | ................ | C12Q 1/28 |
| | | | | 435/25 |
| 2003/0138959 A1* | 7/2003 | Carter | ................ | G01N 21/31 |
| | | | | 436/43 |
| 2014/0073043 A1* | 3/2014 | Holmes | ............ | G01N 33/5005 |
| | | | | 435/287.3 |

* cited by examiner

| ADULTERANT | Specific Gravity INDEX (SGI) | % ABOVE 0.035 CUTOFF |
|---|---|---|
| UNADULTERATED | | |
| Potassium Nitrite (Klear) | 0.019 | 0% |
| Liquid-Plumr® | 0.019 | 0% |
| Baking Soda | 0.019 | 0% |
| Table Salt | 0.019 | 0% |
| ADULTERATED 1% W/V | | |
| Potassium Nitrite (Klear) | 0.385 | 10% |
| Liquid-Plumr® | 0.517 | 48% |
| Baking Soda | 0.637 | 82% |
| Table Salt | 0.643 | 84% |
| ADULTERATED 5% W/V | | |
| Potassium Nitrite (Klear) | 0.0590 | 186% |
| Liquid-Plumr® | 0.844 | 1,263% |
| Baking Soda | 0.1081 | 2,239% |
| Table Salt | 0.1087 | 2,288% |

REAGENTS AND METHODS OF USE WITH AUTOMATED ANALYZERS FOR OBTAINING A SPECIFIC GRAVITY INDEX FOR URINE

CROSS-REFERENCE TO A RELATED APPLICATION

This application claims the benefit of U.S. Provisional Application Ser. No. 62/363,421, filed Jul. 18, 2016, the disclosure of which is hereby incorporated by reference in its entirety, including all figures, tables and drawings.

BACKGROUND OF INVENTION

Drug abuse is a critical problem throughout the world. Commonly abused drugs include cocaine, cannabinoids, amphetamines, and phencyclidine (PCP), as well as designer drugs such as 3,4-methelenedioxyamphetamine ("meth") and 3,4-methelenedioxy-methamphetamine ("Ecstasy").

On Sep. 15, 1986, President Ronald Reagan issued Executive Order No. 12564 directing federal agencies to achieve a drug-free work environment. The Department of Health and Human Services (HHS) has developed guidelines and protocols for drugs-of-abuse testing. It is estimated that approximately 20 million employees are screened each year for illicit drug use. Drug testing programs in the United States can be classified as mandatory or non-mandatory. In the mandatory programs (e.g., the Department of Transportation), a regulated employer is required by federal regulation to test employees. In the non-mandatory programs, employers choose to test for reasons other than federal regulations.

Persons using drugs may attempt to adulterate urine specimens to avoid detection. Adulterants are substances that can be added to, for example, a urine sample to change the integrity of the sample. Some other types of adulterants can be used to mask that a sample has been diluted and can cause a laboratory test to fail in detecting that the sample was diluted. These adulterants are often oxidants that have been shown to destroy, or to partially destroy, evidence of drugs of abuse (DOA) in a urine sample. Thus, both screening and confirmatory tests can be rendered negative.

Oxidant adulterants include potassium nitrite (e.g., "Klear" and "Whizzies"), potassium chlorochromate (e.g., "Urine Luck™") and hydrogen peroxide/peroxidase (e.g., "Stealth") and are readily available, usually at low cost. Household bleach is also an effective adulterant that can cause negative DOA results. Adulterants can degrade and disappear in a sample within hours after being added, making them difficult or impossible to detect. Further, specific tests have to be conducted to detect each type of adulterant.

DOA testing often involves several steps, which can include: (a) sample collection, (b) sample integrity testing, (c) DOA screening, and (d) confirmatory testing. These steps may: (a) occur at different locations, (b) be conducted by personnel with varying qualifications, (c) be conducted by different institutions, and/or (d) be conducted sequentially at different times. For example, confirmatory tests are conducted after the screening tests and often require that the sample be transported from one institution or laboratory to another. The steps leading to the confirmatory testing step may occur over one or more days.

Laboratories typically screen samples using commercially available Enzyme Immunoassays (EIA) and related methods and reagents. These screening methods are not always specific, as there can be cross-reacting substances that cause false positive results. Consequently, cut-off values or minimum concentrations for each drug have been established, whereby assay values below the cut-off value are considered negative results. If a positive result is obtained by the EIA screen, the sample can be sent to a confirmatory testing laboratory where Gas Chromatography/Mass Spectrometry equipment is often utilized for the confirmatory test.

Generally, the cut-off values used for the confirmatory test are lower than the values used for the initial screening (e.g., the EIA). In general, only initially positive screening tests are submitted for confirmatory testing and the confirmatory test results are considered conclusive. Because of the cut-off value criteria used to establish a positive result, adulterants only need to lower the tested value of the urine sample below the cut-off level to produce a negative result.

Clinical laboratory professional organizations have called attention to the problems with adulterated urine samples for illicit drug testing, but detecting an adulterated urine sample is difficult. The American Journal of Clinical Pathology concluded that new adulterants can produce false negative results for DOA. The Substance Abuse and Mental Health Services Administration (SAMHSA) reports that of 6,320,000 samples tested in 2013 one of every 300 was invalid. If the adulterant testing procedures failed to detect "disappearing" adulterants, that number may have been even higher. The invalid tests may also be much higher in non-mandated labs or other labs not performing adequate tests for adulterants.

Manual spot tests have become available to test for the presence of adulterants in a sample. Although a step in the right direction in detecting adulterants, these tests can be laborious and expensive to perform and primarily provide only qualitative results, which may still result in under-detection or false positives. The high cost of these manual tests may lead non-mandated laboratories to take short cuts in adulterant testing, partially because reimbursement for adulterant testing has at times been insufficient. Adulterant testing products and labor can be costly, and the cost is escalating, causing non-mandated laboratories to forego adulterant testing. Ironically, clinical laboratory testing costs in general are one of the few areas in health care where costs of an individual diagnostic test have declined since the 1950's. That reduction in cost has been brought about by laboratory automation and the integration of the automation with laboratory/hospital information systems. The use of automated systems and methods, and the use of reagents, combined with automated sample identification and documentation by an integrated Laboratory Information System computer would enable the costs to be reduced to a fraction of the costs of manual adulteration spot test, if a reagent were available.

Several sample integrity tests are recommended by laboratory professional organizations and government oversight groups. These tests are intended to detect adulteration that destroys drugs, adulteration that interferes with testing, and adulteration by dilution or sample substitution. The principal tests recommended are: temperature measurement—intended to detect sample substitution; pH measurement—intended to detect substances that interfere with testing; specific gravity—intended to detect sample dilution and substances that interfere with testing; and creatinine assay—intended to detect dilution. Additionally, oxidant and aldehyde tests are intended to detect substances known to destroy drugs of abuse.

All of these tests have specific purposes in detecting adulteration of samples. The purpose of the specific gravity test is typically to corroborate the results of prior tests that indicate one of many substances may have been used to adulterate the sample. One of the most common tests for specific gravity involves measuring weight per unit volume (w/v), usually using a mechanical hydrometer placed in an aliquot of the sample. Refractive Index based Specific gravity detectors are also available; however, both of these methods tend to be cumbersome and labor intensive. None of these methods can be used with standard automated laboratory equipment or clinical analyzers. Important record keeping is also laborious, prone to errors, and expensive.

Water is the most common adulterant or dilution agent used to lower levels of drugs in a sample, thereby causing a false negative drug test. Water may be added at the time of collection or by ingestion of a liter or more of water prior to sample collection. The components in urine found in the highest concentrations and that contribute most to the specific gravity of urine are sodium chloride and potassium chloride salts. Urea is also a major contributor to the specific gravity of urine. Specific gravity testing, which relies on one or more of these components, has been shown to be a poor test for detecting sample dilution, particularly in comparison to methods that utilize creatinine measurement. This is because the addition of simple table salt to a urine sample can sufficiently mask the effects of dilution.

In addition, confirmatory laboratory tests are often conducted one or more days following the initial screening test. Urea is known to degrade over a period of one or more days. This degradation involves converting one molecule of urea into two molecules of ammonia and one molecule of carbon dioxide. This degradation can increase the specific gravity of a urine sample, which can also mask any prior dilution of the sample with water.

Recently, reagent strips have become available that can provide an index of specific gravity by measuring the sodium content of the urine. These strips may be less sensitive to ammonia from urea degradation; however, the sodium-detecting reagent strips typically employ a pH indicator dye, which is affected significantly by change in pH resulting from the levels of ammonia. While the strips do not measure the ammonia released by urea degradation, the pH change associated with the urea degradation can affect results, particularly in tests conducted later by confirmatory laboratories. Further, tests performed with reagent strips must be done manually, not with automated laboratory equipment, and the strips do little to solve the testing accuracy and data management costs of conducting tests.

There are commercially available reagents that can be used in automation equipment or clinical analyzers for conducting specific gravity testing on urine samples. These reagents usually depend upon the detection of chloride to derive an index of specific gravity, or a specific gravity derived from just the chloride constituent in a urine sample. Although chloride detection can provide a reasonably accurate index of specific gravity on normal or unadulterated samples, the use of chloride detection to derive specific gravity can be a poor indicator of adulterated samples. This is because some of the most common adulterants contain no chloride and produce no change in the chloride concentration in the sample. Therefore, while the specific gravity of the sample may change, the change will not be detected by these types of chloride-detecting reagents.

Some of the principal adulterants known to affect specific gravity are baking soda (sodium bicarbonate/sodium carbonate), liquid drain openers (sodium hydroxide), Klear (potassium nitrite), and Urine Luck™ (potassium chlorochromate), none of which contain chloride.

Other reagents used in automated analyzers to determine a specific gravity index contain ferric perchlorate or mercury, which is highly toxic. Perchlorate can also be combustible. These issues raise serious questions as to the safety and effectiveness of using these reagents in automated analyzers for the detection of adulteration.

The use of DOA continues to be a problem around the world. The ability to determine whether an individual is using or has used a DOA can be a critical safety issue. Acquiring a urine sample from individuals to be tested is the most expedient and least invasive way to obtain a testable bodily fluid. While there are a variety of screening tests that can be conducted to try to detect DOA in a urine sample, many are inaccurate or are not sufficiently reliable to be considered undeniable confirmation. Confirmatory testing can be used to try to corroborate samples with a positive screening test. One of the most common tests conducted by confirmatory laboratories is measuring specific gravity or, more specifically, an index of specific gravity based on one or more constituents in the urine. Unfortunately, these tests have not been entirely reliable and changes in the urine sample over time can affect the results of testing for an index of specific gravity.

Compounding the historical reliability questions surrounding the use of prior specific gravity tests is the fact that drug users wanting to subvert DOA sample integrity testing receive advice from internet sites. Most DOA testing labs currently perform creatinine assays as a means of detection invalid sample integrity due to dilution. Commonly, specific gravity tests are only performed if the creatinine concentration of a sample is below 20 mg/dL. Although creatinine has historically been the gold standard for the detection of dilution, new subversion techniques, such as in vivo dilution, are now being used to subvert detection. The technique of in vivo dilution was first discovered in studies athletes and body builders who often take, a.k.a. "load", supplemental creatine to increase muscle mass. Creatine is converted in muscle to creatinine, which is excreted in the urine. [Schedel J, Tanaka M, Tanaka H, Kiyonaga M. et al. Consequences of one-week creatine supplementation on creatinine levels in athletes' serum and urine, Schweizerische Zeitschrift für <<Sportmedizin and Sporttraumatologie>> 2000; 48: 111-116.] Information can also be obtained from the World Wide Web that provides advice about how to "load" with creatine and protein, consume large amounts of water prior to the test, and perform exercise to obtain both a normal urine creatinine and specific gravity while still diluting DOA below detection cut off levels. There remains a need for safe, effective reagents for measuring specific gravity of a urine sample. Furthermore, the ability to use such reagents in automated clinical analyzers would provide a quicker and more cost effective method for conducting confirmatory urine tests to detect DOA.

BRIEF SUMMARY

The subject invention provides methods and reagents useful for analysis and measurement of specific constituents in a urine sample that can be used to derive a Specific Gravity Index (SGI) for a urine sample. When the SGI of a given urine sample is compared to the SGI of known normal urine samples, results can be used to determine whether the given sample was adulterated, typically, in an effort to mask use of Drugs-of-Abuse (DOA). In particular, the subject invention provides reagents and methods for the measurement of specific markers normally present in a urine sample, where such markers can be useful indicators for detecting adulteration of the sample.

Beneficially, the reagents and methods of the subject invention can be used with standard laboratory automation equipment or clinical analyzers to measure the markers in the given sample, thereby facilitating automated urine sample analysis for detection of adulteration.

Specifically, spectrophotometry analysis of a sample treated with a reagent of the subject invention can provide a quantitative measurement of specific markers that can be used to derive a SGI for the sample. Abnormal SGI measurements can be an indication that the sample has been adulterated by dilution or addition of another substance, such as salt, which can alter the specific gravity of the sample. More specifically, spectrophotometry analysis of a sample treated with a reagent of the subject invention can be used to determine a SGI for the sample, which, if outside of an accepted normal range for the SGI, would indicate that the integrity of the sample was compromised.

Specific gravity is a measure of the weight of a liquid divided by the weight of water. The constituents found in the highest concentrations in urine are sodium chloride and potassium chloride and, as such, contribute most to the specific gravity measurement for a urine sample. However, there are other constituents, such as urea, which also contribute to the overall specific gravity of a urine sample. A Specific Gravity Index, (SGI), according to the subject invention, is a measurement obtained by utilizing a subset of the constituents found in a urine sample. More specifically, the SGI is a measurement of the weight of the non-aqueous constituents of the sample per unit volume. Advantageously, the subset of constituents can also be used as markers, according to the subject invention, for automating analysis of a urine sample, so as to obtain a SGI.

One embodiment of the subject invention utilizes the sodium (Na+) and potassium (K+), naturally found in a urine sample, as markers. In a further embodiment, these same markers are used to obtain a SGI for the sample. In a specific embodiment, a sodium-potassium dependent β-Galactosidase is utilized along with an indicator chromogen of o-nitrophenylgalactoside (o-NPG). In one embodiment, the method of the subject invention results in the formation of a yellow color due to cleavage of the o-NPG into o-nitrophenol, a molecule that can be analyzed by the spectrophotometry methods utilized in most clinical analyzers to obtain a SGI for the given sample. The chromogen can be cleaved to o-nitrophenol by using the sodium or potassium activated β-Galactosidase. Thus, the amount of sodium and/or potassium in a given urine sample can dictate the amount of cleaved o-NPG created by the reaction. Magnesium, Mg++ has also been known to activate β-galactosidase; however, the amount of Mg++ in a urine sample is significantly less than the amount of Na+ or K+.

The amount of yellow o-nitrophenol that is produced from the colorless o-NPG can be measured spectrophotometrically at a primary wavelength of 405 nm-410 nm. The rate of increase in absorbance at 405 nm-410 nm is proportional to total sodium and potassium concentration in the sample. Light absorbance measurements outside a known normal range of a SGI for urine can be an indication of abnormal levels of sodium and/or potassium in the sample. This can be an indication that the sample integrity has been compromised.

Many of the current methodologies measure the amount of chloride in a urine sample, where the amount of chloride detected can be used as an indication of adulteration; however, many of the products used to adulterate urine samples do not contain chloride. Thus, their addition to a urine sample may have no effect on the total chloride amounts. Advantageously, by utilizing the total amount of sodium and potassium, to obtain a SGI, instead of attempting to directly detect the amount of chloride in the sample, the reagent and methods of the present invention can be used to indicate more generally whether the sample has been adulterated.

If it can be determined initially that the sample has been adulterated in a fashion that has affected the SGI, remaining automated tests can be halted and another sample obtained as soon as possible. This can save time and resources, and may aid in obtaining an unadulterated sample in time to determine whether DOA have been used.

Specific gravity measurement of urine samples is used by testing laboratories. Currently, the adulteration of samples capable of being detected by a Specific Gravity measurement can be divided into two types: (a) sample dilution, which can cause a low sample specific gravity; and (b) sample adulteration, such as, for example, by addition of salt, which can cause a higher than normal specific gravity. Of these two types, adulteration by addition of substances to the sample that causes a higher than normal specific gravity can be the most important. This is because it has been determined that detection of sample dilution is more accurately detected by methods that measure the amount of urine creatinine. Current methodology requires that a specific gravity measurement to detect dilution of a sample need only be performed if the creatinine level is below a certain threshold, such that measurement of specific gravity on such samples can provide a corroborative indication of dilution. Among routine integrity tests, certain adulterants can only be detected by a specific gravity measurement.

The present invention employs a unique and advantageous departure from currently known technologies for the measurement of sodium. Further, according to the novel concepts of the present invention, both sodium and potassium, which are normally present in urine, can be used in a single test yielding a total sodium and potassium value. The total sodium and potassium value can then be used to calculate a SGI, utilizing an automated analysis system.

In one embodiment of the subject invention, a given urine sample, or portion thereof, is combined with a pre-determined amount of o-nitrophenylgalactoside (o-NPG), which is normally colorless. The treated sample can be reacted with β-galactosidase, which, in the presence of the sodium and potassium in the urine, will cleave the o-NPG into o-nitrophenol. The amount of cleavage is dependent upon the amount of sodium and potassium in the urine sample. The resulting O-nitrophenol has a yellow color that intensifies with concentration. Analysis of the reacted sample by spectrophotometry can yield a measurement of the mEq/L of total sodium and potassium in the urine sample, which can be converted to provide an SGI for the sample. If the calculated SGI is outside the normal range for urine, then it can be presumed that the sample was subject to tampering.

Specific gravity testing is used as one of the principal means, along with pH and creatinine measurement, for detecting tampering or adulteration of samples submitted for DOA testing. However, the process of obtaining specific gravity is time-consuming, expensive, and prone to error. It is a goal of the present invention to provide reagents and methods for obtaining instead a Specific gravity Index (SGI), which can be optimized for the detection of sample tampering. It is also a goal of the subject invention to utilize automated testing devices and techniques for the analysis of urine by measuring the normally occurring substituents of sodium (Na+) and potassium (K+) as indicators of adulteration or tampering with a urine sample.

Magnesium (Mg++) is also known to activate β-galactosidase. Human urine contains approximately 1 mMol/L of Mg++. This is significantly less than the amount of sodium and potassium normally present in urine, though still likely to be sufficient to activate the β-Galactosidase in the reagent of the subject invention. However, as with the sodium and potassium, dilution of a urine sample will also equally dilute the magnesium and thus reduce activation of β-galactosidase. Thus, the overall effect of magnesium on the SGI obtained by the methods of the subject invention is minimal. However, it has been observed that inclusion of magnesium in the reagent and calibrators, in a ratio normal to the sodium and potassium in urine, can improve sensitivity to effects of urine dilution.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. Thus, understanding that these drawings depict only typical embodiments of the invention and are not therefore to be considered as limiting in scope, the invention will be described and explained with additional specificity and detail through the use of the accompanying drawings in which.

DETAILED DISCLOSURE

Figures 1, 2:
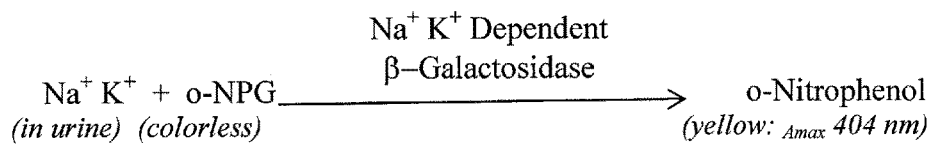
FIG. 1 is an equation showing one embodiment of the reaction method of the subject invention.
FIG. 2 is a table showing the results of the Specific gravity Index (SGI) measurements on normal urine samples and samples adulterated with common adulterants. Typically, the effects of an adulterant are not measurable below 10% w/v. It can be seen that, with embodiments of the subject invention, adulterant concentrations in a sample of 1% and 5% w/v can be detected and indicate the sample is positive for adulteration. This indicates a high sensitivity for this test.
Figure 3:
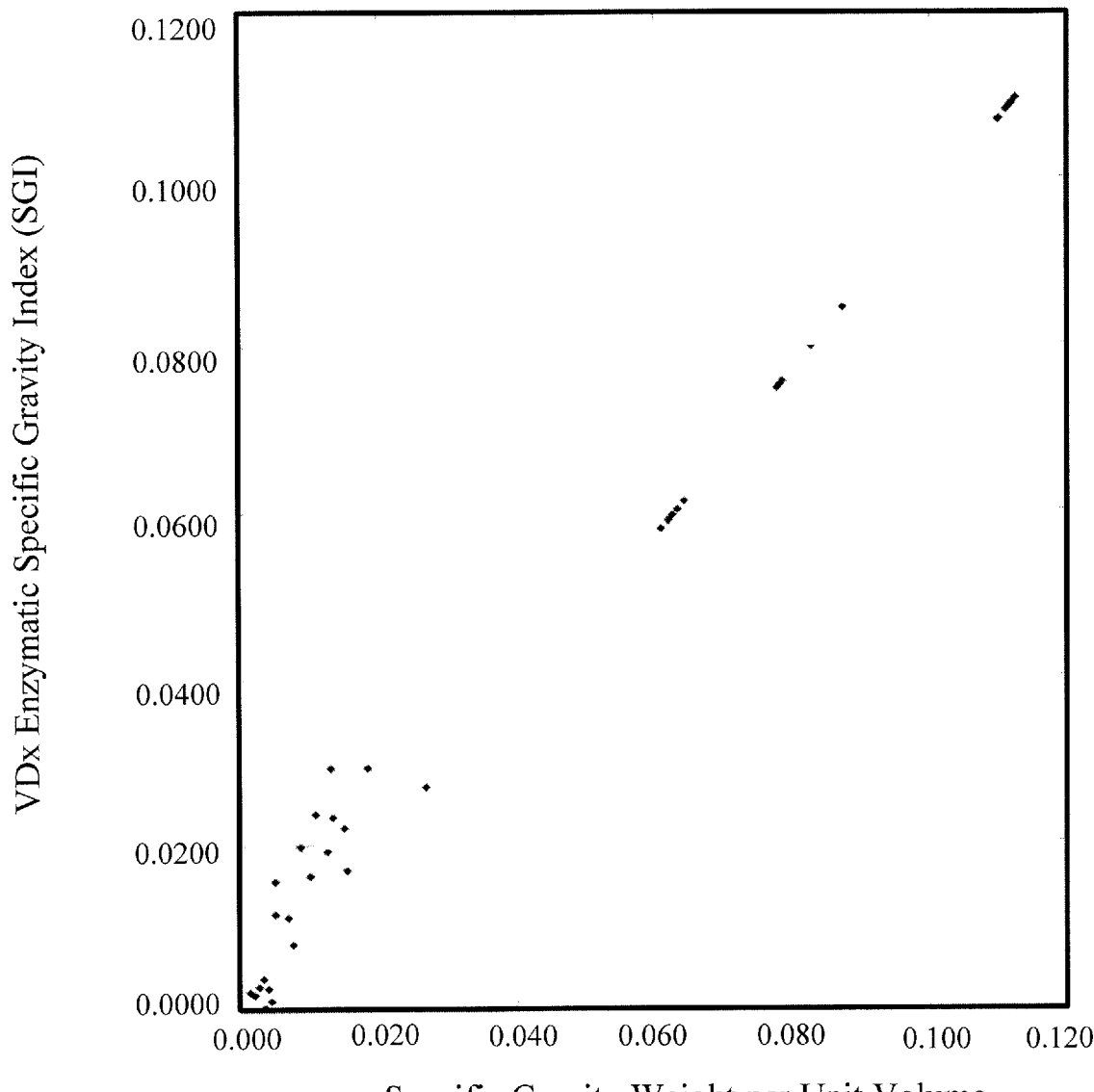
FIG. 3 is a graph comparing the actual specific gravity of urine samples to the Specific gravity Index of the subject invention. The regression analysis statistics are also provided.

The subject invention pertains to an assay reagent and methods of use for determining whether a urine sample, usually one submitted for drugs-of-abuse (DOA) testing, has been subject to tampering. The assay can utilize the sodium and the potassium in a urine sample as markers for obtaining a Specific gravity Index (SGI), where such measurement can be useful for determining whether a urine sample has been adulterated in a fashion that changes the actual specific gravity of the sample. Advantageously, the reagents utilized according to the subject invention are safe and relatively non-toxic. The embodiments of the subject invention are further advantageous in that they can be incorporated for use with standard automated laboratory equipment, such as clinical analyzers, and the procedures utilized to conduct automated testing of urine samples.

While the subject application describes, and many of the terms herein relate to, a use for detecting adulteration of urine samples in a fashion intended to mask DOA, other modifications apparent to a person with skill in the art and having benefit of the subject disclosure are contemplated to be within the scope of the present invention. For example, embodiments of the subject invention can be useful for detecting disease, dietary issues, or health-related problems.

The embodiments of the subject invention are useful for obtaining a SGI for a urine sample. Regular specific gravity (SG) testing has been used as one of the principal methods, along with pH and creatinine measurement, for detecting sample tampering or adulteration of samples submitted for DOA testing. While SG is a measure of all of the constituents in urine, the SGI of the subject invention relies on a measurement of a subset of those constituents, specifically sodium and potassium. The SGI can then be used to determine whether the urine sample exhibits a normal range of sodium and potassium. If the SGI is outside the normal range for urine, adulteration can be suspected and the sample can be subjected to additional more specific tests for adulteration or, alternatively, further testing on the sample can be halted and another sample obtained.

One advantage of the subject invention is that it has the ability to utilize not only substances normally found in human urine, but those which are also affected by efforts to alter the specific gravity of urine, usually in an attempt to mask use of DOA. A further advantage of the subject invention is the ability to utilize automated laboratory equipment and clinical analyzers to obtain the SGI of a urine sample. The liquid reagents of the subject invention can be utilized in such equipment and the sample can be further analyzed utilizing the spectrophotometry capabilities present in such equipment, making the analysis procedure efficient, economical, and accurate.

According to embodiments of the subject invention, both sodium and potassium in an aliquot of a urine sample can be measured by a single test yielding a total sodium and potassium value for the sample. In one embodiment, the SGI is a measure of the concentration of these non-aqueous components per unit volume. Most adulterants will affect the concentration of one of these constituents. The total sodium and potassium value can then be used to calculate a SGI. In one embodiment, reagents and methods are provided that can be used for measuring the total sodium and potassium, which can be used to obtain a Specific gravity Index, as indicator of potentially adulterated samples. A measured Specific gravity Index outside the normal range for human urine can be presumed as adulterated or subjected to tampering.

In a specific embodiment, the reagent and method of the present invention employ sodium-potassium dependent beta-galactosidase (β-galactosidase) in conjunction with an indicator chromogen of o-nitrophenylgalactoside (o-NPG). The reaction causes the chromogen to be cleaved into o-nitrophenol by the sodium and/or potassium activated β-galactosidase. Advantageously, the rate at which the yellow o-nitrophenol is produced from the colorless o-NPG can be measured spectrophotometrically at a primary wavelength of 405-410 nm. FIG. 1 illustrates this reaction.

Utilizing the spectrophotometry results, a measurement of both sodium and potassium, can be extrapolated to yield a total mEq/L of both substances in the sample. Unlike specific gravity detection methods that rely on the measurement of chloride, the total sodium-potassium as mEq/l that can be obtained with the reagent and method of the subject invention is affected by a variety of commonly used adulterants. Such adulterants can include, but are not limited to, baking soda (sodium bicarbonate/sodium carbonate), liquid drain openers (sodium hydroxide), Klear (potassium nitrite), Urine Luck™ (potassium chlorochromate), and common table salt. Note that none of these common adulterants contain chloride. Thus, addition of such adulterants to a urine sample would likely not be detectable by current specific gravity measuring techniques.

FIG. 2 illustrates the sensitivity of the method of the subject invention. The typical tests used for detecting a non-normal specific gravity, such as "dipsticks" that rely upon the amount of sodium, are usually not effective where the w/v of adulterant in a sample is below 10%. FIG. 2 demonstrates that embodiments of the subject invention are capable of detecting adulteration of only 5% w/v and even as little as 1% w/v, for the most common adulterants.

As mentioned above, in one embodiment the reagent used in the method of the subject invention produces a yellow coloration to the aliquot of the urine sample being tested. More specifically, the cleavage of the o-nitrophenylgalactoside (o-NPG) into o-nitrophenol can produce a yellow coloration in the aliquot. The amount of coloration imparted to the sample aliquot is dependent upon the amount of sodium and potassium present in the sample to activate the β-galactosidase. Therefore, it is possible to utilize high urine to reagent ratio to ensure that the SGI for a sample aliquot is not inadvertently truncated due to insufficient reagent. In one embodiment, the sample aliquote:reagent ratio is between approximately 1:20 to approximately 1:100. In a more specific embodiment, the sample aliquote:reagent ratio is between approximately 1:50 and approximately 1:80.

The mean sodium level in normal urine has been reported to be about 115 mEq/L with a range of between approximately 20 mEq/L and approximately 230 mEq/L based upon 5,474 samples. [Bhusman Kapur et al.: "Urine Fingerprinting—Detection of Sample Tampering in Opiate Dependency Program" Ther Drug MON, 21: 243-250, (1999)]. The Tietz Textbook (Clinical Chemistry and Molecular Diagnostics, Burtis, C. A, et al., eds. $5^{th}$ Edition, St. Louis: Elsevier Saunders; 2011) gives the relative percentage of total sodium and potassium in urine to be approximately 36.84% potassium and approximately 63.16% sodium. Thus, the calculated Mean Total of combined sodium and potassium found in normal human urine is about 198 mEq/L with a range of between approximately 32 mEq/L and approximately 364 mEq/L Utilizing these percentages, the range for a normal SGI can be calculated as being between approximately 32 mEq/L and approximately 364 mEq/L. Thus, a combined Total Sodium and Potassium Value, which is the total amount of sodium and potassium in a urine sample, yielding a SGI below 32 mEq/L can be indicative of sample dilution and a SGI over 364 mEq/L can be indicative of adulteration.

Specific gravity is a dimensionless quantity. As such, the mEq/L units of total sodium and potassium when converted gives a SGI of 0.003 for the 32 mEq/L low-end cut-off value reagent calibrator and a SGI of 0.035 for the 264 mEq/L high end cut-off value reagent calibrator. When measuring specific gravity, the decimal value is the specific gravity of a substance minus the specific gravity of $H_2O$, which should be 1.0000. Embodiments of the subject invention provide a Specific gravity Equivalent Value, based on the substituents of sodium and potassium in a urine sample, which can be calculated by adding 1 to the decimal value of the SGI. The currently recommended low specific gravity limit is 1.003 and the recommended high specific gravity limit is 1.035. Thus, for the purposes of automation and recording, it can be necessary to convert the SGI by adding 1.0 to the decimal value.

Alternatively, SGI can be calculated as the weight per unit volume of the non-aqueous constituents of a sample divided by the specific gravity of water, which is 1.0000 mg/mL. Thus, when the combined Total Sodium and Potassium Value is used, the SGI can range from between approximately 0.0030 and approximately 0.0350. A SGI below 0.0030 can be indicative of dilution of the sample and a SGI above 0.0350 can be indicative of adulteration. As mentioned above, embodiments of the subject invention can be incorporated with automated laboratory equipment that is typically used for urine sample aliquot analysis. In one embodiment, the β-galactosidase and the o-NPG can be formulated as a single reagent, such that the reaction can be conducted as a single step. In an alternative embodiment, the β-galactosidase and the o-NPG can be formulated as separate reagents, such that the reaction is carried out in two or more steps.

The equipment currently found in most laboratories utilizes a method based on a fixed time calculation of the rate of color formation at a wavelength of 405-410 nm. In other words, all samples are analyzed at a pre-determined fixed time and at a pre-determined wavelength. The automated equipment must also be calibrated initially and periodically during testing to ensure accuracy. The automated equipment can be calibrated with a high end value reagent, a low end value reagent, and a reagent blank to obtain a two-point linear calculation against which the tested samples can be compared.

Potassium chloride and sodium chloride, in the molar concentrations discussed above, can be formulated in an aqueous solution by a person of skill in the art to obtain an appropriate calibrator. In addition, 0.2% ProClin™ 300 can be used as a stabilizer for the aqueous calibrator. The stabilized calibrator can be used with automated machinery, such as clinical analyzers, to calibrate the high end cut-off value of 264 mEq/L and can be appropriately diluted to also calibrate the low end cut-off value of 32 mEq/L. Thus, a urine sample with an SGI above or below this range can be considered adulterated or tampered with in some manner.

One embodiment of the subject invention provides a liquid regent that can be added to an aliquot of a urine sample to initiate the yellow color change in the sample aliquot. The formulation for the reagent is prepared as follows:

Reagent Concentrations

| | |
|---|---|
| beta-Galactosidase | 25 to 8000 U/L |
| ortho-NPG | >0.2 mM |
| buffer | pH 7-9.5 |
| $Mg^{2+}$ | .01-10 mmol/L |
| EGTA (free acid) | 1-20 mmol/L |
| Serum Albumin | 0-5 g/L |
| N-Acetyl Cystine | 0.05-2M |
| ProClin 300 ® | 2 grams/L |

The ingredients should preferably be salt free, particularly with regard to heavy metals, calcium, sodium and potassium. It can also be desirable for pH adjustments to be made on aliquots of the reagent. Ideally, such aliquots are discarded in order to minimize potassium contamination of the reagent.

Urine typically contains calcium, which can vary between samples. Calcium can be a competitive inhibitor of the activation of beta-galactosidase by magnesium also present in the urine. Calcium is also unstable and can affect stability of the reagent. In one embodiment, EGTA is utilized in a reagent of the subject invention to complex calcium in the urine sample. The amount necessary will depend upon the amount of calcium that needs to be deactivated in a given sample. In the embodiment shown above, approximately 0.5-20 mmol/L are utilized. It is within the skill of person trained in the art to determine the appropriate amount of EGTA that may be required for a particular sample. Such variations which provide the same functionality, in substantially the same way, with substantially the same result are within the scope of this invention.

In an alternative embodiment, which can be useful in automation equipment, the ortho-nitrophenylgalactoside (o-NPG) can be provided as a second reagent of known concentration that can be added to the first regent to achieve the desired final concentration indicated above.

The stability of the o-NPG containing second reagent can be maximized by adjusting pH to be about 6.5. Ideally, a minimal amount of buffer is used to achieve this pH, so that when the second reagent is added to the first reagent, there is minimal or no effect on the final reaction pH, which should be about 8.5.

The addition of magnesium to the calibrators and controls in proportion to their concentration relative to mean normal specific gravity index can improve sensitivity to the effect of dilution, or measurements at the lower cut-off value of 0.0030 SGI. In one embodiment, the amount of magnesium utilized in a reagent of the subject invention is between approximately 0.01 mmol/L to approximately 0.01-2 mmol/L. In a more particular embodiment, the amount of magnesium utilized in a reagent of the subject invention is between approximately 0.01 mmol/L to approximately 1 mmol/L.

Prior to analysis, the analyzer can be calibrated. This can be done with a reagent blank, a low end calibrator having a sodium and potassium concentration that is at or near the normal low range limit in human urine and the high end calibrator having a sodium and potassium concentration that is at or near the normal high range limit in human urine. In one embodiment, the low end calibrator contains approximately: 20 mEq/L of sodium chloride and 11.7 mEq/L of potassium chloride. In a further embodiment, the high end calibrator contains approximately 230 mEq/L of sodium chloride and 134 mEq/L of potassium chloride.

Specific Gravity Indexes of 0.0000 (deionized water) and 0.0030 can be used for the low end calibrators and a specific gravity of 1.0350 can be used for the high end calibrator. To produce more quantitative results over a broader range, calibrators of 0.0000 (deionized water), 0.0030 (low cut off for dilution), a mid-calibrator of 0.019, a high cut-off calibrator for salting of 0.0350, and a high range calibrator of 0.050 can be used.

In one embodiment, the decimal portion of these Specific gravity Indexes can be used for automation purposes, e.g., 0.003 and 0.035, so as to produce the Specific Gravity Decimal. Most clinical/biochemistry analyzers allow the inclusion of a constant for outputting results. For example, the Beckman AU400 series of analyzers provides a "Correlation Factor". Setting the correlation factor B to 1.0 produces values which add the weight of water to the result so that 0.0030 becomes 1.0030 which is the value with which physicians are accustomed. The Mindray BS200 provides a "Compensate" in its parameter settings and setting the intercept to 1.0 produces values which add the weight of water to the result so that 0.0030 becomes 1.0030.

The reagent system of the subject invention is intended for use on automatic analyzers, such as enzyme immunoassay analyzers, such as the Mindray BS200 Clinical Analyzer. In one embodiment, the reagent can be used with these types of equipment in the following manner: 5 µl aliquot of a urine sample is placed in a sample tube and mixed with 180 µl of the first reagent. This can be mixed with 72 µl of the second reagent. The instrument spectrophotometer can be set at 405 nm, and the calibrator values of the instrument can be set at 1.003 for the normal low end and 1.035 for the normal high end. The absorbance of the sample aliquot can then be measured.

The reagent embodiments of the subject invention, when mixed with an adulterated urine sample will result in a yellow coloration to the sample, the intensity of which depends upon the specific gravity (ionic strength) of the solution. While such color change may be observable in manual inspection, it is particularly suited for detection by automatic analyzers, especially those with spectrophotometric capabilities.

Following are specifications for running urine samples through several different immunoassay type of analyzers, including the Mindray BS-200 and the Beckman Coulter AU400, AU400e, AU480, AU640, AU640e and AU680 Series Clinical Chemistry Analyzers. The settings shown are intended to be guidelines for the indicated instruments. It is within the skill of a person trained in the art to recognize that such parameters will vary between instruments.

Assay Parameter Settings for Mindray BS-200 Analyzer
Test: SGI
No. User Defined
Full Name: Specific Gravity Index
Reaction Type: Fixed-time
Pri. Wave 405 nm
Sec Wave 510 nm
Direction: Increase
Reac. Time: 0 and 9
Incubation Time: 3
Unit: g/mL
Precision: 0.0001
R1: 250
R2: 100
Sample Volume; 4
Compensate: Slope: 1 Intercept: 1.0
Calibration Parameters
Rule Logit-Log 5P
Replicates 1
Determination coeff. 0
Calibrators: 0.0000 (deionized water), 0.0030 (low cut off for dilution), a mid-calibrator of 0.019, a high cut-off calibrator for salting of 0.0350, and a high range calibrator of 0.0500

Assay Parameter Settings for Beckman Coulter AU400, AU400e, AU480, AU640, AU640e and AU680 Series Clinical Chemistry Analyzers
Reagent ID: User defined
Test Name: Specific Gravity Index
Sample Volume: 2
R1 Volume: 107
R2 Volume: 43

|  | Correlation factor | |
| --- | --- | --- |
|  | A 1.0 | B 1.0 |
| Wavelength: Pri: | 410 Sec. | 600 |
| Method: | FIXED | |
| Reaction Slope: | + | |
| Measuring Point 1: | First 11 | Last 26 |
| Measuring Point 2: | (Not Applicable) | |
| Calibration Type: | 5AB | Formula: Polygonal Counts 1 CONC |
| Point 1 H20 | 0.0000 | |
| Point 2 Low C/O | 0.0030 | |

| Correlation factor | |
|---|---|
| A 1.0 | B 1.0 |
| Point 3 MID | 0.0190 |
| Point 4 Hi C/O | 0.0350 |
| Point 5 Hi Range | 0.0500 |

Following are examples that illustrate procedures for practicing the subject invention. These examples are provided for the purpose of illustration only and should not be construed as limiting. Thus, any and all variations that become evident as a result of the teachings herein or from the following examples are contemplated to be within the scope of the present invention.

Example 1: Measurement of Creatinine as Validation of Specific Gravity Index (SGI) Method to Detect Dilution of Urine It is not uncommon for urine samples to be diluted with water or another substance in an effort to dilute or mask Drugs of Abuse (DOA). This can most often be detected by methods that measure the creatinine levels in the urine. The measurement of creatinine levels in a urine sample is currently accepted as the gold standard for determining whether a sample has been diluted. Current government regulations mandate that the cut-off level for determining whether a sample has been diluted is 20 mg/dL. Thus, any sample presented that is measured with a creatinine level below 20 mg/dL is considered compromised by dilution.

Samples having a below-normal creatinine level can be further tested by measuring the specific gravity of the sample. Current tests for specific gravity are determined by measuring the uric acid levels in a sample and extrapolating a value from that measurement. If the specific gravity of a sample is measured to be below 1.0030, the sample is deemed as being abnormal or having been subjected to tampering. However, it has been shown that current methods for measuring specific gravity cannot be correlated to the creatinine levels of a sample. Thus, it is possible for a sample to have a positive indication of dilution by creatinine measurements and a negative indication of dilution by specific gravity measurement. (Kaput, B. M., "2007, "Frequently Asked Questions, Opiate Dependency and Methadone Maintenance Treatment Program follow-up"; found at: http://www.cpso.on.ca/getattachment/CATs/CPSO-Members/Related-Links-Methadone-Program/Opiate-Dependency-FAQS_Kapur.pdf.aspx).

A study was conducted to determine whether the Specific gravity Index method of the subject invention could be correlated to the creatinine levels in urine samples. Random urine samples were obtained and the creatinine levels were measured for each sample. The creatinine measurements for all of the samples ranged from 31 mg/dL to 253 mg/dL. The samples were then diluted from between 3.2% to 88.1%, depending upon the sample, to achieve creatinine levels of 10.0 mg/dL, 20 mg/dL, and 30 mg/dL.

The diluted samples were then assayed using a Mindray BS-200 analyzer. Tables 1, 2, and 3 show the results of the assay tests. Table 1 shows that for 100% of the samples diluted to creatinine levels of <20 mg/dL, the Specific Gravity Index (SGI) values were less than the 1.0030 cutoff level for dilution. The mean SGI value for these samples was 1.002. Table 2 shows that for 100% of the samples diluted to creatinine levels of >20 mg/dL, the SGI values were greater than the 1.0030 cutoff level for dilution. The mean value for these samples was 1.007. Table 3 shows that for the samples diluted to creatinine levels of at or near 20 mg/dL, the SGI values for most of the samples were near the 1.0030 cutoff level for dilution. The mean value was exactly 1.0030 with a Standard Deviation of 0.0007.

TABLE 1

| Sample | Creatinine mg/dL | Specific gravity Index (SGI) | SGI Result |
|---|---|---|---|
| 1 | 10 | 0.0009 | Positive for dilution |
| 2 | 10 | 0.0013 | Positive for dilution |
| 3 | 10 | 0.0014 | Positive for dilution |
| 4 | 10 | 0.0013 | Positive for dilution |
| 5 | 10 | 0.0012 | Positive for dilution |
| 6 | 10 | 0.0014 | Positive for dilution |
| 7 | 10 | 0.0010 | Positive for dilution |
| 8 | 10 | 0.0014 | Positive for dilution |
| 9 | 10 | 0.0013 | Positive for dilution |
| 10 | 10 | 0.0012 | Positive for dilution |
| 11 | 10 | 0.0016 | Positive for dilution |
| 12 | 10 | 0.0016 | Positive for dilution |
| 13 | 10 | 0.0019 | Positive for dilution |
| 14 | 10 | 0.0018 | Positive for dilution |
| 15 | 10 | 0.0018 | Positive for dilution |
| 16 | 10 | 0.0020 | Positive for dilution |
| 17 | 10 | 0.0016 | Positive for dilution |
| 18 | 10 | 0.0020 | Positive for dilution |
| 19 | 10 | 0.0020 | Positive for dilution |
| 20 | 10 | 0.0019 | Positive for dilution |
| 21 | 10 | 0.0018 | Positive for dilution |
| 22 | 10 | 0.0019 | Positive for dilution |
| 23 | 10 | 0.0021 | Positive for dilution |
| 24 | 10 | 0.0018 | Positive for dilution |
| 25 | 10 | 0.0019 | Positive for dilution |
| 26 | 10 | 0.0020 | Positive for dilution |
| 27 | 10 | 0.0019 | Positive for dilution |
| 28 | 10 | 0.0020 | Positive for dilution |
| 29 | 10 | 0.0019 | Positive for dilution |
| 30 | 10 | 0.0016 | Positive for dilution |
| 31 | 10 | 0.0019 | Positive for dilution |
| 32 | 10 | 0.0020 | Positive for dilution |
| 33 | 10 | 0.0021 | Positive for dilution |
| 34 | 10 | 0.0020 | Positive for dilution |
| 35 | 10 | 0.0022 | Positive for dilution |
| 38 | 10 | 0.0021 | Positive for dilution |
| 39 | 10 | 0.0014 | Positive for dilution |
| 40 | 10 | 0.0012 | Positive for dilution |

0.002 = Average

TABLE 2

| Sample | Creatinine mg/dL | Specific gravity Index (SGI) | SGI Result |
|---|---|---|---|
| 41 | 20 | 0.0021 | Borderline |
| 42 | 20 | 0.0026 | Borderline |
| 43 | 20 | 0.0036 | Normal |
| 44 | 20 | 0.0020 | Borderline |
| 45 | 20 | 0.0023 | Borderline |
| 46 | 20 | 0.0032 | Normal |
| 47 | 20 | 0.0038 | Normal |
| 48 | 20 | 0.0034 | Normal |
| 49 | 20 | 0.0035 | Normal |
| 50 | 20 | 0.0036 | Normal |
| 51 | 20 | 0.0021 | Borderline |
| 52 | 20 | 0.0023 | Borderline |
| 53 | 20 | 0.0030 | Borderline |
| 54 | 20 | 0.0024 | Borderline |
| 55 | 20 | 0.0021 | Borderline |
| 56 | 20 | 0.0037 | Normal |
| 57 | 20 | 0.0010 | Borderline |
| 58 | 20 | 0.0033 | Normal |
| 59 | 20 | 0.0027 | Borderline |
| 60 | 20 | 0.0022 | Borderline |
| 61 | 20 | 0.0020 | Borderline |

TABLE 2-continued

| Sample | Creatinine mg/dL | Specific gravity Index (SGI) | SGI Result |
|---|---|---|---|
| 62 | 20 | 0.0025 | Borderline |
| 63 | 20 | 0.0031 | Normal |
| 64 | 20 | 0.0028 | Borderline |
| 65 | 20 | 0.0029 | Borderline |
| 66 | 20 | 0.0035 | Normal |

0.003 = Average
0.0007 = SD

TABLE 3

| Sample | Creatinine mg/dL | Specific gravity Index (SGI) | SGI Result |
|---|---|---|---|
| 67 | 30 | 0.0058 | Normal |
| 68 | 30 | 0.0057 | Normal |
| 69 | 30 | 0.0072 | Normal |
| 70 | 30 | 0.0073 | Normal |
| 71 | 30 | 0.0072 | Normal |
| 72 | 30 | 0.0073 | Normal |
| 73 | 30 | 0.0074 | Normal |
| 74 | 30 | 0.0072 | Normal |
| 75 | 30 | 0.0068 | Normal |
| 76 | 30 | 0.0069 | Normal |
| 77 | 30 | 0.0067 | Normal |
| 78 | 30 | 0.0066 | Normal |
| 79 | 30 | 0.0065 | Normal |
| 80 | 30 | 0.0063 | Normal |
| 81 | 30 | 0.0062 | Normal |
| 82 | 30 | 0.0060 | Normal |
| 83 | 30 | 0.0063 | Normal |
| 84 | 30 | 0.0063 | Normal |
| 85 | 30 | 0.0061 | Normal |
| 86 | 30 | 0.0072 | Normal |
| 87 | 30 | 0.0069 | Normal |
| 88 | 30 | 0.0069 | Normal |
| 89 | 30 | 0.0071 | Normal |
| 90 | 30 | 0.0076 | Normal |
| 91 | 30 | 0.0061 | Normal |
| 92 | 30 | 0.0054 | Normal |
| 93 | 30 | 0.0069 | Normal |
| 94 | 30 | 0.0077 | Normal |
| 95 | 30 | 0.0072 | Normal |
| 96 | 30 | 0.0052 | Normal |

0.007 = Average

For Tables 1, 2, and 3:
Catalog No. V-ASG
R1 LOT: 1614
R2 LOT: 1618
Pre-Dilution Range of Creatinine=31-253 Mg/dL
Dilution range: 3.2%-88.1%

The data indicate that the Specific gravity Index method of the subject invention is accurate for testing samples for dilution and may be superior to the current methods of detecting specific gravity, including methods that utilize weight per unit volume. The embodiments of the reagents and methods of the subject invention were tested with synthetic urine having a Specific Gravity Index (SGI) less than the dilution cut off of 0.0030, a creatinine greater than 20 mg/dL and a mean normal urea level. The SGI method and reagents were effective at indicating an abnormal or diluted sample. Both creatinine assay and specific gravity measurement by standard refractometer methods usually fail to detect the abnormal diluted samples, whereas the SGI test of the subject invention can effectively detect in vivo dilution with a creatine/protein/water/exercise regimen, which the currently used methods are inhibited from detecting.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

I claim:

1. An assay method for spectrophotometrically analyzing a urine sample with a clinical analyzer, the assay method comprising:
    combining the urine sample with a liquid reagent comprising β-galactosidase and o-nitrophenylgalactoside that react with sodium and potassium in the urine sample to form o-nitrophenol in a reacted urine sample at a rate that is proportional to the combined molar concentration of sodium and potassium in the urine sample, wherein the clinical analyzer is programmed to correlate the rate of formation of o-nitrophenol in the reacted urine sample to a Total Sodium and Potassium Value that is equivalent to the combined molar concentration of the sodium and potassium in the urine sample;
    wherein the clinical analyzer is further programmed to,
    analyze the reacted urine sample spectrophotometrically for a period of time to obtain a measure of the rate of increase in light absorbance corresponding to the rate of formation of o-nitrophenol in the reacted urine sample;
    convert the measure of the rate of increase in light absorbance to an amount of o-nitrophenol formed in the reacted urine sample; and
    correlate the rate of formation of o-nitrophenol to the corresponding Total Sodium and Potassium Value for the urine sample.

2. The assay method according to claim 1, wherein the rate of formation of o-nitrophenol is spectrophotometrically measured between 405 nm and 410 nm.

3. An assay method for use with a clinical analyzer to obtain a Specific Gravity Index for a urine sample, the method comprising:
    combining the urine sample with a first reagent comprising β-galactosidase;
    combining the urine sample with a second reagent comprising o-nitrophenylgalactoside, which is converted to o-nitrophenol in a reacted urine sample at a rate that is proportional to a combined molar concentration of sodium and potassium present in the urine sample;

analyzing with a spectrophotometer of the clinical analyzer the reacted urine sample to obtain a measure of the rate of increase in light absorbance of the o-nitrophenol formed in the reacted urine sample, wherein the clinical analyzer is programmed to correlate the measure of the rate of increase in light absorbance of o-nitrophenol to the combined molar concentration of sodium and potassium in the urine sample and provide a Total Sodium and Potassium Value and;

converting, with the programmed clinical analyzer, the Total Sodium and Potassium Value to the Specific Gravity Index.

4. The assay method according to claim 3, wherein the rate of increase in light absorbance of o-nitrophenol is spectrophotometrically measured between 405 nm and 410 nm.

5. The assay method according to claim 1, further comprising the programmed clinical analyzer calculating a Specific Gravity Index utilizing the Total Sodium and Potassium Value wherein the specific gravity of water (1.0) is added to the Total Sodium and Potassium Value.

6. The assay method, according to claim 5, wherein a Specific Gravity Index below 1.0030 or above 1.035 is indicative of adulteration of the urine sample.

7. The assay method according to claim 6, further comprising obtaining a measure of creatinine in the urine sample spectrophotometrically with the clinical analyzer, wherein a measure of creatinine below 20 mg/dL is further indicative of adulteration of the urine sample.

8. The assay method according to claim 1, wherein the reagent system further comprises N-acetyl cysteine.

9. The assay method according to claim 3, wherein a Specific Gravity Index below 1.0030 or above 1.035 is indicative of adulteration of the urine sample.

10. The assay method according to claim 9, further comprising obtaining a measure of creatinine in the urine sample spectrophotometrically with the clinical analyzer, wherein a measure of creatinine below 20 mg/dL is further indicative of adulteration of the urine sample.

11. The assay method, according to claim 1, further comprising calibrating the clinical system with a reagent calibrator that comprises magnesium.

12. The assay method, according to claim 3, further comprising calibrating the clinical analyzer with a reagent calibrator that comprises magnesium.

13. The assay method, according to claim 1, wherein the urine sample and liquid reagent system are combined in a ratio of at least approximately 1:20, at least approximately 1:50, at least approximately 1:80, or at least approximately 1:100.

14. The assay method, according to claim 1, wherein the β-galactosidase and o-nitrophenylgalactosidase are in separate reagents that are subsequently combined with the urine sample.

15. The assay method according to claim 3, wherein at least one of the first reagent and the second reagent further comprises N-acetyl cysteine.

16. The assay method according to claim 1, further comprising calibrating the clinical analyzer with at least a high-end reagent calibrator comprising a Total Sodium and Potassium Value of 264 mEq/L and a low-end reagent calibrator comprising a Total Sodium and Potassium Value of 32 mEq/L.

17. The assay method according to claim 3, further comprising calibrating the clinical analyzer with at least a high-end reagent calibrator comprising a Total Sodium and Potassium Value of 264 mEq/L and a low-end reagent calibrator comprising a Total Sodium and Potassium Value of 32 mEq/L.

* * * * *